(12) United States Patent
Struck

(10) Patent No.: US 6,197,760 B1
(45) Date of Patent: Mar. 6, 2001

(54) ISOPHOSPHORAMIDE MUSTARD ANALOGS AND USE THEREOF

(75) Inventor: Robert F. Struck, Birmingham, AL (US)

(73) Assignee: Southern Research Institute, Birmingham, AL (US)

(*) Notice: Subject to any disclaimer, the term of this patent is extended or adjusted under 35 U.S.C. 154(b) by 0 days.

(21) Appl. No.: 09/577,349

(22) Filed: May 24, 2000

Related U.S. Application Data

(60) Provisional application No. 60/135,830, filed on May 24, 1999.

(51) Int. Cl.[7] .................. A61K 31/664; A61P 35/00; C07F 9/22
(52) U.S. Cl. ............................... 514/126; 558/45
(58) Field of Search ................ 514/126; 558/45

(56) References Cited

FOREIGN PATENT DOCUMENTS 51-059886 * 5/1976 (JP).

OTHER PUBLICATIONS

Voelcker, G. et al. Structure/activity studies with thiazolidinyl–and perhydrothiazinyl–phosphamide esters. Journal of Cancer Research and Clinical Oncology 1998, vol. 124, Issue 6, pp. 297–300.*
STN International, CAPLUS Database, Chemical Abstracts Service, (Columbus, Ohio), Accession No. 1976:463098 (1978); abstract of JP 51–059886.*

* cited by examiner

Primary Examiner—Michael G. Ambrose
(74) Attorney, Agent, or Firm—Connolly Bove Lodge & Hutz

(57) ABSTRACT

Isophosphoramide mustard analogs useful for treating cancer are provided.

12 Claims, 1 Drawing Sheet

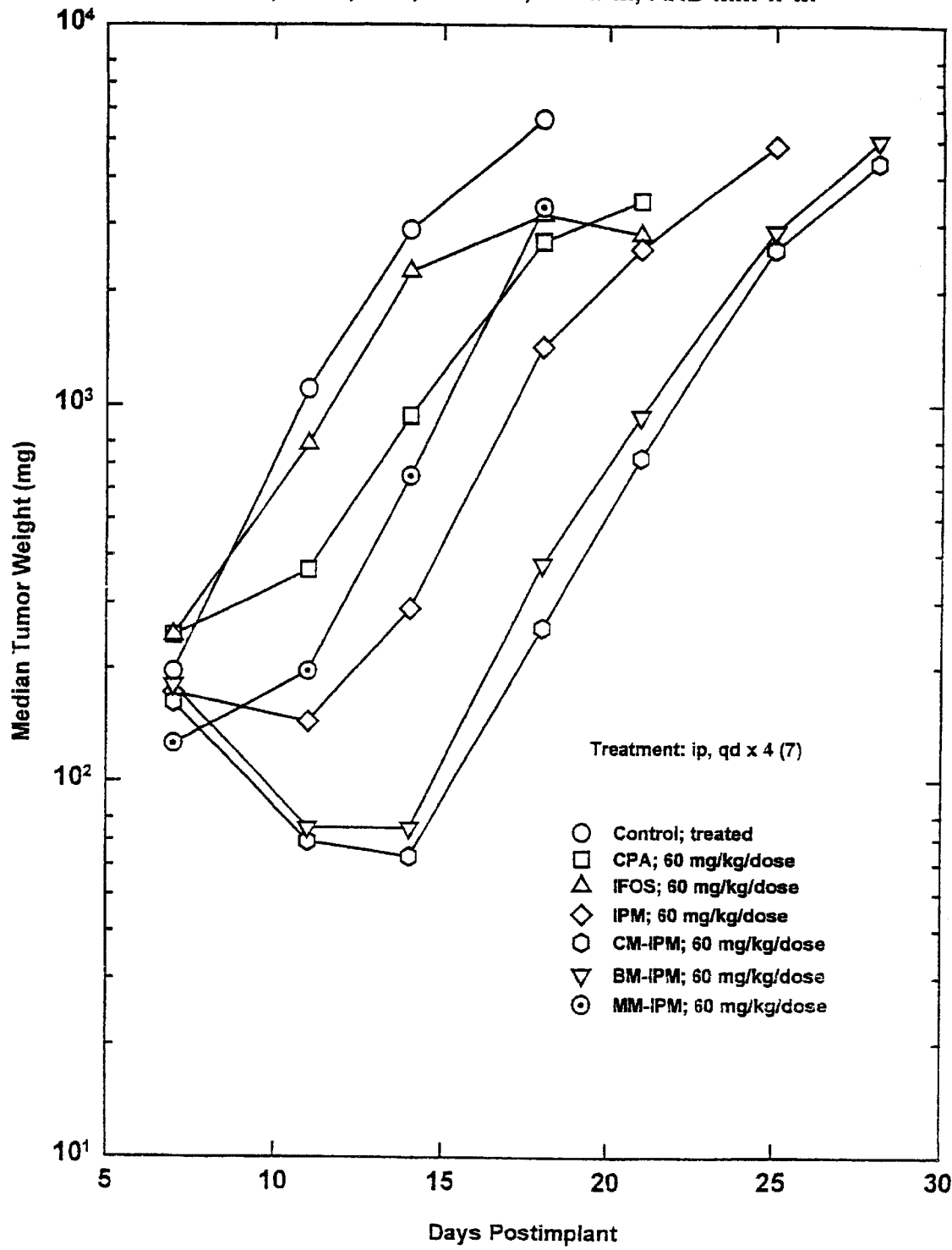

ISOPHOSPHORAMIDE MUSTARD ANALOGS AND USE THEREOF

This application claims the benefit of U.S. Provisional Application No. 60/135,830, filed May 24, 1999.

DESCRIPTION

Federally Sponsored Research and Development

This invention was supported by Grants R01 CA 35812 and PO1 CA 34200 from the National Cancer Institute, National Institutes of Health and, therefore, the U.S. Government might have a paid-up license in this invention and the right in limited circumstances to require the patent owner to license others on reasonable terms as provided for by the terms of Grants RO1 CA 35812 and PO1 CA 34200.

1. Technical Field

The present invention relates to certain analogs of isophosphoramide mustard (also referred to herein as IPM). The present invention also relates to pharmaceutical compositions comprising the compounds of the present invention, as well as a method of using the compounds in treating cancer in a mammal.

2. Background of Invention

Even though significant advances have occurred in the treatment of cancer, it still remains a major health concern. It has been reported that cancer is the cause of death of up to one of every four Americans.

At the present time, cyclophosphamide (CPA) is the most widely used agent of the alkylating agent class in the clinical treatment of cancer. Two congeners, ifosfamide (Ifos, Holoxan®) and trofosfamide (Trofos, Ixoten®) are also in clinical use in the U.S. and/or Europe. CPA is particularly advantageous in the clinical treatment of ovarian and breast cancer, while Ifos is effective in the clinical treatment of testicular cancer and soft tissue sarcomas. Ifos is also being used in the clinical treatment of breast cancer in the combination drug regimen ICE (Ifos, carboplatin, etopside), since breast cancer is sensitive to Ifos, even occasionally when patients have not responded to CPA-based treatment, suggesting the possibility of some lack of cross resistance between these two drugs. The metabolic pathway for Ifos is shown in Scheme 1 and the metabolic pathway for CPA is closely similar to the Ifos pathway.

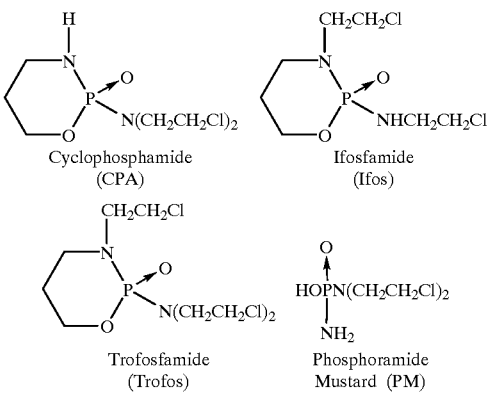

Cyclophosphamide (CPA)

Ifosfamide (Ifos)

Trofosfamide (Trofos)

Phosphoramide Mustard (PM)

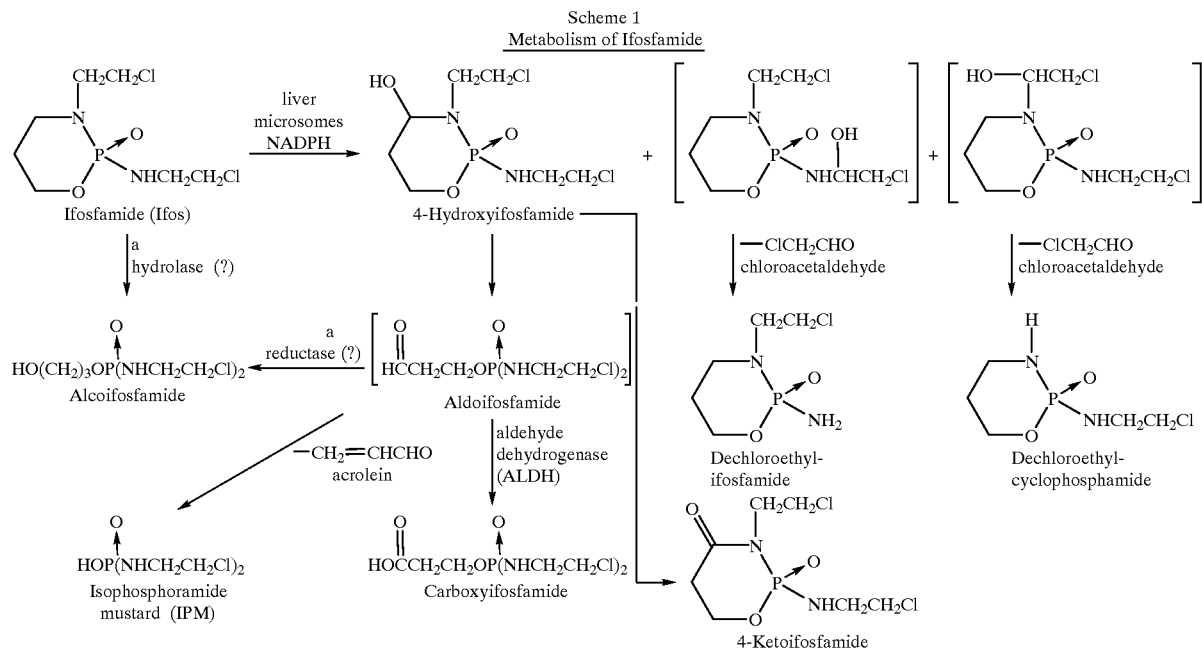

Scheme 1
Metabolism of Ifosfamide

IPM has been identified as a major metabolite in patients treated with Ifos. It possesses a spectrum of therapeutic efficacy generally comparable to that of CPA and Ifos against experimental leukemias and solid tumors in mice and rats, as illustrated in Tables 1 and 2. It is important to note that PM is inferior to IPM against experimental solid tumors (Table 2). One limited clinical trial (Phase I) with PM has been reported, and three objective responses were observed (Nathanson et al., *Cancer Chemother. Rep.* 51:35–39, 1967).

TABLE 1

Activity of Isophosphoramide Mustard Against L1210/0 and L1210/CPA Leukemias
(Optimal Response at ≦ LD10 Dose, from Dose-response Study)

| | | L1210/0[†] Tumor burden at start of Treatment = 8.5 × 10⁸ cells | | | L1210/CPA[†] Tumor burden at start of Treatment = 6.0 × 10⁷ cells | | |
|---|---|---|---|---|---|---|---|
| Agent | MTD Dosage* (mg/kg$^{-1}$) | Day 60 survivors/ total | % ILS (dying mice only) | Net log$_{10}$ reduction in tumor burden after therapy | Day 60 survivors/ total | % ILS (dying mice only) | Net log$_{10}$ reduction in tumor burden after therapy |
| Cyclophosphamide | 200 | 0/10 | +107 | 7 | 0/10 | +57 | 4 |
| Ifosfamide | 431 | 0/10 | +185 | 8 | 0/10 | +85 | 5 |
| | 289 | 0/9 | +114 | 8 | 0/10 | +57 | 4 |
| Isophosphoramide mustard | 100 | 0/10 | +128 | 8 | 1/10 | +114 | 7 |

*Treatment: i.p.; day 2 only; highest non-toxic dose (LD$_{10}$ or less, MTD) in a range of doses.
[†]Implant: i.p.; 10⁶ cells, in male CDF$_1$ mice.

TABLE 2

Response of Lewis Lung Carcinoma to Isophosphoramide Mustard
Implant Size: 20–30 mg; Implant Site: s.c.; Drug Treatment: i.p.

| Agent | Schedule | Highest non-toxic dosage (MTD) (mg kg$^{-1}$/dose) | Tumour-free survivors | % ILS[‡] | Log kill total[δ] |
|---|---|---|---|---|---|
| Cyclophosphamide (CPA) | Day 2 Single dose | 200 | 5/10 | 68 | >6.8 |
| Ifosfamide (Ifos) | Day 2 Single dose | 300 | 7/10 | 55 | >4.5 |
| Phosphoramide (PM) mustard | Day 2 Single dose | 200 | 0/10 | 15 | 1.2 |
| | Day 2 Q5 min × 7 | 30 | 0/10 | 17 | 1.5 |
| Isophosphoramide Mustard (IPM) | Day 2 Single dose | 100 | 6/10 | 34 | >2.1 |

[‡]Increase in life span, excluding survivors.
[δ]The Log$_{10}$ cell kill (total) was calculated from the following formula: Log kill = T C value/ (3.32 T$_4$). Where T$_4$ is the tumour volume-doubling time measured from a best fit straight line of the control-group tumours in exponential growth (100 400 mg range). T$_4$ = 1.2 for Lewis tumour in this experiment.
Comment: The observation of a 50–70% cure rate for CPA, Ifos and IPM agents indicates equivalent activity at equal host toxicity.

Another important consideration is the toxicity of CPA and Ifos. Their common dose limiting toxicity in patients is hemorrhagic cystitis, the cause of which has been attributed to a metabolite, acrolein, generated on the activation pathway (Scheme 1). Much effort has been expended on effective means of controlling this manifestation of high-dose CPA and Ifos. Acrolein has also been shown to be responsible for possible liver toxicity in the form of glutathione depletion and destruction of mixedfunction oxidase activities (cytochrome P-450, aryl hydrocarbon hydroxylase, aminopyrinedemethylase). Furthermore, acrolein was shown to be a teratogenic metabolite of CPA, and 4-hydroxy-CPA, the primary metabolite of CPA in the activation pathway, was shown to be a more potent mutagen than PM. This may be related to a more serious side effect of CPA and its congeners, i.e., bladder cancer; several reports link CPA therapy with subsequent bladder carcinoma and other malignancies, including leiomyosarcoma of the bladder, Hodgkins lymphoma, and acute myeloid leukemia, and acrolein has been proposed as a co-carcinogen in the etiology of such tumors arising in patients after CPA treatment.

Several clinical toxicities in addition to cystitis have also been attributed to Ifos, notably encephalopathy and renal toxicity. The causative metabolite in CNS toxicity has been suggested to be chloroacetaldehyde.

However, the above-discussed acrolein induced toxicities can be avoided by using IPM or a congener. Also, chloroacetaldehyde mentioned above is a metabolite that is not likely to be readily derivable from IPM or an analog. Therefore, IPM or a congener having anticancer activity would provide certain advantages over Ifos and CPA.

Another possible advantage of IPM or a congener over Ifos and CPA is that patient variability in activation of Ifos or CPA would be eliminated. Although this weakness cold be overcome by dose escalation until comparable hematologic toxicity is observed, it is probably true that many clinicians treat with historically-established doses and, if typical toxicity is not observed, may or may not escalate doses in future treatment. In either case, time is lost for patients who metabolize Ifos or CPA less efficiently than normal, and these patients may be compromised to further chemotherapy with these or other agents because of some toxicity and the possible initiation of development or selection of resistant tumor cells.

Further, direct administration of IPM or an analog would circumvent a CPA- and Ifos-type susceptibility to resistance mediated by tumor cell aldehyde dehydrogenase (ALDH) in tumors in which levels of this enzyme are effective in detoxifying aldophosphamide or aldoifosfamide. The obvious negative aspect of this phenomenon is that normal tissues will be more susceptible to typical alkylating agent toxicity, which manifests itself principally as hematologic toxicity. However, selectivity remains, as illustrated by the results shown in Table 1 and 2, in which comparable antitumor activity at equal toxicity (MTD, LD10) was observed, and by the fact that IPM was judged by the National Cancer Institute to have clinical potential. However, the clinical effectiveness of IPM has not been reported.

Finally, there could also be an economic advantage. Ifos is currently used in most sarcoma, lymphoma and germ cell carcinoma protocols. Ifos still produces hematuria despite normal precautions. If the added expense and time to properly administer Ifos and prevent toxicities could be eliminated by replacement of Ifos with IPM or a congener, the improved economics would be a major accomplishment.

Accordingly, a number of analogs of IPM have been prepared and particularly the following analogs:

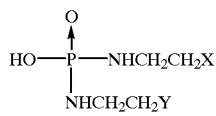

BB-IPM: X = Y = Br
FF-IPM: X = Y = F
MM-IPM: X = Y = mesyloxy ($OSO_2CH_3$)
BC-IPM: X = Br, Y = Cl
CF-IPM: X = Cl, Y = F
FM-IPM: X = F, Y = mesyloxy
C-BS-IPM: X = Cl, Y = butanesulfonyloxy ($OSO_2(CH_2)_3CH_3$)
$CM^3$-IPM: X = Cl, Y = $CH_2OSO_2CH_3$ The synthesis of IPM, MM-IPM, BB-IPM and BC-IPM has been reported by Rauen and Schriewer, *Arznein. Forsch.* 21: 518–524, 1971 and Studzian et al., *Biochem Pharmacol.* 43: 937–943, 1992. No antitumor cytotoxicity data were reported for IPM or MM-IPM, but BB-IPM and BC-IPM were observed to be cytotoxic to HeLa cells in vitro.

It would therefore be desirable to develop a compound(s) which exhibits antitumor cytotoxicity but does not suffer from the disadvantages of using Ifos and/or CPA as discussed above.

SUMMARY OF INVENTION

The present invention relates to certain analogs of IPM which exhibit antitumor activity. The compounds of the present invention exhibit the following advantages over Ifos and CPA: 1) no variability in plasma levels of the active metabolite as a result of patient variability in metabolism, 2) no acrolein is produced (implicated in dose limiting hemorrhagic cystitis and cytochrome P450 deactivation), 3) no chloroacetaldehyde (a metabolite implicated in Ifos CNS toxicity) is produced, and 4) no susceptibility to ALDH-mediated tumor cell resistance is possible, with the major disadvantage being related to this latter advantage in the loss of an ALDH-protective mechanism in normal tissue.

In particular, the present invention relates to compounds represented by the formula:

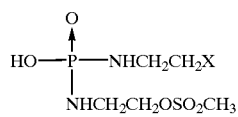

wherein X is Cl or Br.

The present invention also relates to a pharmaceutical composition comprising at least one of the above-disclosed compounds and a pharmaceutically acceptable carrier.

The present invention also relates to treating cancer in a mammal by administering an effective cancer treatment amount of at least one of the above-disclosed compounds.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

SUMMARY OF DRAWINGS

The FIGURE is a graph showing response of tumor to compounds of the present invention compared to compounds outside the scope of the present invention.

BEST AND VARIOUS MODES FOR CARRYING OUT INVENTION

The present invention relates to compounds represented by the formula:

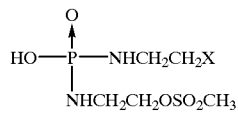

wherein X is Cl or Br and is preferably Cl.

The compounds of the present invention can be prepared by the following synthesis route:

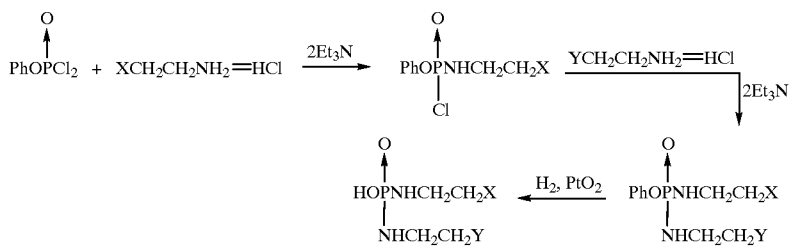

wherein X is Cl or Br and Y is $OSO_2CH_3$.

The following non-limiting example illustrates the general procedure for preparing compounds of the present invention:

EXAMPLE 1

Phenyl phosphorodichloridate is treated with one equivalent of the appropriate 2-substituted-ethylamine hydrochloride. The mixture is cooled to 0° C. and treated dropwise with stirring with two equivalents of triethylamine. The mixture is allowed to warm to room temperature and is stirred for two hours at this temperature. One equivalent of the second 2-substituted-ethylamine hydrochloride is added, the mixture is cooled to 0° C. and treated dropwise with stirring with two equivalents of triethylamine. This mixture is allowed to warm to room temperature and is stirred for two more hours. The mixture is washed twice with water, and the methylene chloride solution is dried over sodium sulfate, filtered and evaporated to dryness. The resulting syrup residue is analyzed by mass spectroscopy and thin layer chromatography (TLC) to confirm the presence of the appropriate phenyl phosphorodiamidate. Following confirmation, the residue is separated by preparative TLC to isolate the purified product, which is reduced in a Parr shaker apparatus in dioxane at 50 psig pressure in the presence of platinum oxide catalyst for one hour. Filtration yields a filtrate and a product-catalyst mixture, which is washed with methanol to solubilize the precipitated product. The dioxane-methanol filtrate is concentrated in vacuo to a small volume, and typically (as experienced with the analogs prepared to date), the pure, crystalline product is collected by filtration, dried in vacuo, and characterized by mass and NMR spectroscopy and by elemental analysis.

If the product does not precipitate, the filtrate is evaporated to dryness and the residue triturated with ether to remove unreduced starting material and filtered. The residue, if not analytically pure, will be crystallized from acetone-methanol.

2-Sulfonyloxy-ethylamine hydrochlorides can be prepared by converting ethanolamine to its N-CBZ derivative, purifying by column chromatography with purity confirmed by TLC, reaction with one equivalent of the appropriate sulfonyl chloride in methylene chloride at 0° C. followed by dropwise addition of one equivalent of triethylamine, stirring one hour at 0° C. and one hour at room temperature, washing with water, drying over sodium sulfate, and evaporation to dryness to yield a syrup, which is purified by column chromatography or preparative TLC. The purified product is characterized by TLC and mass and NMR analysis. The resulting N-CBZ derivative in dioxane in the presence of one equivalent of concentrated hydrochloric acid and 10% Pd/C catalyst is hydrogenated in Parr shaker apparatus for one hour at 15 psig pressure, and the mixture is filtered. The filtration residue (catalyst and ppt.) is washed with MeOH and filtered. Evaporation of the combined dioxane-methanol filtrate to dryness in vacuo yields the 2-mesyloxyethylamine hydrochloride in sufficient purity and yield for use as described above.

The following examples illustrate the antitumor activity of CM-IPM and BM-IPM in vivo:

EXAMPLE 2

Experimental Tumor Models

The antileukemic activity of CM-IPM and BM-IPM was evaluated vs. murine leukemia P388 in comparison to IPM, MM-IPM and two other analogs, and the results are shown in Table 3 below revealing superior activity for CM-IPM (6.1 log cell kill) and BM-IPM (5.5 log cell kill) in comparison to IPM and MM-IPM, both of which produced 4.8 log cell kill.

TABLE 3

Evaluation of Five Mesyloxy Analogs of IPM Against I.P. Implanted P388 Leukemia

| Treatment: IP; Q1DX1 (1) | | | | Therapeutic Response Approx. Net | | |
|---|---|---|---|---|---|---|
| Agent | Name | Dosage (Mg/kg) Dose | 45-Day Surv/Total | Median Day of Death | % ILS | Log10 Change In Tumor Burden at End of Rx |
| Control | (Untreated) |  | 0/20 | 11.0 |  |  |
| CM-IPM |  | 100 | 0/5 | 20.0 | +82 | −6.1 |
| BM-IPM |  | 100 | 0/5 | 19.0 | +73 | −5.5 |
| FM-IPM |  | 100 | 0/5 | 13.0 | +10 | −1.4 |
| CM3-IPM |  | 100 | 0/5 | 12.0 | +9 | −0.7 |
| MM-IPM |  | 100 | 0/5 | 18.0 | +64 | −4.8 |
| NSC 297900 | IPM | 100 | 1/5 | 18.0 | +64 | −4.8 |

Activity was also evaluated vs. murine M5076 sarcoma, and the results are shown in Table 4 revealing superior activity for CM-IPM (23.2 days T-C) in comparison to 7.2 days for BM-IPM and 6.1 days for IPM.

TABLE 4

Response of S.C. Implanted M5076 Sarcoma to Treatment with CM-IPM, BM-IPM and IPM

| Agent | Dose (mg/kg) | Days to 2 Doublings | Days delay (T-C) | Tumor-free Surv/Total |
|---|---|---|---|---|
| CM-IPM | 40 | 32.5 | 23.2 | 0/6 |
| CM-IPM | 27 | 21.5 | 12.2 | 0/6 |
| CM-IPM | 18 | 11.6 | 2.3 | 0/6 |
| BM-IPM | 40 | Toxic | — | 0/6 |
| BM-IPM | 27 | 16.5 | 7.2 | 0/6 |
| BM-IPM | 18 | 10.1 | 0.8 | 0/6 |
| IPM | 40 | 15.4 | 6.1 | 0/6 |
| IPM | 27 | 12.6 | 3.3 | 0/6 |
| IPM | 18 | 10.3 | 1.0 | 0/6 |

The compounds were injected i.p. daily on days 11–15.

Evaluation vs. the aggressive murine mammary tumor 16/C gave the results shown in the figure in which both CM-IPM and BM-IPM were superior to the clinical drugs CPA and Ifos and to MM-IPM, none of which caused tumor regression, and to IPM, which yielded limited regression.

EXAMPLE 3

Human Tumor Xenograft Models

Evaluations vs. the widely-used s.c.-implanted MCF-7 human mammary tumor xenograft at doses equal to or less than the $LD_{20}$ in a range of doses on a 5-day treatment schedule gave the results shown in Table 5. CM-IPM was equal in activity to Ifos, slightly superior to IPM and melphalan (the positive control) and significantly superior to CPA and all of the other analogs evaluated in the experiment.

TABLE 5

Response of S.C.-Implanted MCF-7 Tumor to Various IPM Analogs

| Agent | Days Delay (T-C) |
|---|---|
| CM-IPM | >39.7 |
| BM-IPM | 4.7 |
| BC-IPM | 5.8 |
| BB-IPM | 1.7 |
| MM-IPM | 4.7 |
| IPM | 33.9 |
| CPA | 6.7 |
| IFOS | >39.7 |
| Melphalan (positive control) | 28.1 |

An analogous experiment vs. MX-1 human mammary tumor xenograft yielded only modest activity for CM-IPM, good activity for BM-IPM and IPM and high activity for CPA and Ifos.

BM-IPM was evaluated vs. human LOX-IMVI melanoma and produced a 52% increase in life span (ILS) and 20% survivors, while IPM yielded an identical ILS with no survivors. CPA was much more active and gave a 121% ILS, although no survivors, as shown in Table 6.

TABLE 6

Evaluation of BM-IPM Against I.P. Implanted Human Lox-IMVI Melanoma

| | Treatment: IP: Q1DX1 (1) | | | Therapeutic Response | |
|---|---|---|---|---|---|
| Agent | Name | Dosage (mg/kg/dose) | 55-Day Surv./Total | Median Day of Death | % ILS |
| Control | (Untreated) | | 0/10 | 19.0 | |
| NSC 26271 | CPA | 40 | 0/5 | 42.0 | +121 |
| NSC 297900 | IPM | 40 | 0/5 | 29.0 | +52 |
| BM-IPM | BM-IPM | 30 | 1/5 | 29.0 | +52 |
| | | 15 | 0/5 | 24.0 | +26 |

The above evaluation of CM-IPM and BM-IPM vs. three experimental leukemias and solid tumors indicated that CM-IPM was superior to IPM and other IPM analogs, including MM-IPM, vs. all three tumors, comparable to BM-IPM vs. 16/C mammary tumor, and superior to CPA and Ifos vs. 16/C tumor. Historically, CPA and Ifos are comparably active to CM-IPM vs. P388 leukemia and M5076 sarcoma.

In the human tumor xenograft models, CM-IPM was superior to MM-IPM, BC-IPM and CPA, slightly more active than IPM, and equally active to Ifos, at equitoxic does $\leq LD_{20}$ vs. MCF-7 mammary tumor and modestly active relative to CPA and Ifos vs. MX-1 mammary tumor, while BM-IPM and IPM were more active but less so than CPA and Ifos, BM-IPM was comparably active to IPM but less active than CPA vs. LOX melanoma, although BM-IPM gave 20% survivors.

In keeping with the present invention, the isophosphamide analogs can be used alone or in appropriate association, and also may be used in combination with pharmaceutically acceptable carriers and other pharmaceutically active compounds such as other cancer treatment drugs. The isophosphoramide mustard analogs also may be used as its alkali, alkaline earth, amine and ammonium salts. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The isophosphoramide analogs alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or watersoluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an animal are available, and, although more than one route can be used to administer a particular compound, a particular route can provide a more immediate and more effective reaction than another route.

The present invention further provides a method of treating cancer in a mammal, especially humans. The method comprises administering an effective treatment amount of the compounds of the present invention to the mammal.

As regards these applications, the present inventive method includes the administration to an animal, particularly a mammal, and more particularly a human, of a therapeutically effective amount of the compound effective in the inhibition of neoplasia and tumor growth.

The compound and compositions of the present invention can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The method of the present invention is particularly applicable in the treatment of brain, colon, renal and mammary tumors, and preferably colon, brain and mammary tumors. The method of the present invention can be practiced on mammals, particularly humans.

The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer, without unmanageable side effects.

The total amount of the compound of the present invention administered in a typical treatment is preferably between about 60 mg/kg and about 2000 mg/kg of body weight for mice, and between about 5 mg/kg and about 100 mg/kg of body weight, and more preferably between 5 mg/kg and about 20 mg/kg of body weight for humans. This total amount is typically, but not necessarily, administered as a series of smaller doses over a period of from about one day to about 24 months, and preferably over a period of 28 days to about 12 months.

The size of the dose also will be determined by the route, timing and frequency of administration as well as the existence, nature, and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method of the present invention comprises further administering of chemotherapeutic agent other than the IPM congeners of the present invention. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozotocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, thioguanine, floxuridine, fludarabine and cladribine.

Examples of chemotherapeutic agents that are natural products include actinomycin D, bleomycin, camptothecins, daunomycin, doxorubicin, etoposide, mitomycin C, TAXOL (paclitaxel), taxotere, teniposide, vincristine, vinorelbine, mithramycin, idarubicin, MITHRACIN™ (plicamycin), deoxycoformycin and L-asparaginase.

An example of a hormonal chemotherapeutic agent includes tamoxifen. Examples of the aforesaid miscellaneous chemotherapeutic agents include mitotane, mitoxantrone, vinblastine, and levamisole.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound represented by the formula

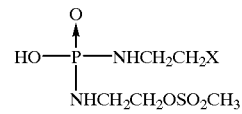

wherein X is Cl or Br.

2. The compound of claim 1 wherein X is Cl.

3. The compound of claim 1 wherein X is Br.

4. A pharmaceutical composition comprising a compound of claim 1 and a pharmaceutically acceptable carrier.

5. A method of treating cancer in a mammal comprising administering to the mammal an effective cancer treatment amount of a compound of claim 1.

6. The method of claim 5, wherein the cancer is selected from the group consisting of mammary tumors, brain tumors, colon tumors, renal tumors, ovarian tumors, neuroblastoma, and retinoblastoma.

7. The method of claim 6 wherein the cancer is selected from the group consisting of mammary tumors, colon tumors, and brain tumors.

8. The method of claim 5 wherein the treatment amount is from about 5 mg/kg to about 200 mg/kg of the body weight of the mammal.

9. The method of claim 8 wherein the treatment amount is from about 5 mg/kg to about 100 mg/kg of the body weight of the mammal.

10. The method of claim 5 wherein the treatment is carried out over a period of from one day to about 24 months.

11. The method of claim 5 wherein the compound is administered orally, intravenously or intraperitoneally.

12. The method of claim 5 wherein the mammal is human.

* * * * *